United States Patent
Kraus et al.

(10) Patent No.: US 11,819,581 B2
(45) Date of Patent: Nov. 21, 2023

(54) TOUCH SCREEN DISPLAY SURFACE SANITIZATION USING ANTIMICROBIAL LIGHT

(71) Applicant: Ecolab USA Inc., St. Paul, MN (US)

(72) Inventors: Paul R. Kraus, Apple Valley, MN (US); Amani Babekir, Greensboro, NC (US); Gina McDowell, Greensboro, NC (US); Teresa C Podtburg, Waconia, MN (US)

(73) Assignee: Ecolab USA Inc., St. Paul, MN (US)

( * ) Notice: Subject to any disclaimer, the term of this patent is extended or adjusted under 35 U.S.C. 154(b) by 220 days.

(21) Appl. No.: 16/918,644

(22) Filed: Jul. 1, 2020

(65) Prior Publication Data
US 2021/0000991 A1    Jan. 7, 2021

Related U.S. Application Data

(60) Provisional application No. 62/870,267, filed on Jul. 3, 2019.

(51) Int. Cl.
*A61L 2/10* (2006.01)
*A61L 2/24* (2006.01)

(52) U.S. Cl.
CPC ..... *A61L 2/10* (2013.01); *A61L 2/24* (2013.01); *A61L 2202/11* (2013.01)

(58) Field of Classification Search
None
See application file for complete search history.

(56) References Cited

U.S. PATENT DOCUMENTS

| | | |
|---|---|---|
| 5,755,103 A | 5/1998 | Na et al. |
| 6,573,663 B1 | 6/2003 | MacGregor et al. |
| 7,270,195 B2 | 9/2007 | MacGregor et al. |
| 8,182,744 B2 | 5/2012 | Mlodzinski et al. |
| 8,398,264 B2 | 3/2013 | Anderson et al. |
| 8,581,882 B2 | 11/2013 | Sohn et al. |
| 9,034,271 B2 | 5/2015 | Shur et al. |
| 9,039,966 B2 | 5/2015 | Anderson et al. |

(Continued)

FOREIGN PATENT DOCUMENTS

| | | |
|---|---|---|
| CN | 101452358 A | 1/2009 |
| CN | 204121454 U | 1/2015 |

(Continued)

OTHER PUBLICATIONS

U.S. Appl. No. 17/325,398, filed May 20, 2021, by Voss et al.

(Continued)

*Primary Examiner* — Andrew Smyth
(74) *Attorney, Agent, or Firm* — Shumaker & Sieffert, P.A.

(57) ABSTRACT

A lighting array including one or more antimicrobial light segments, each light segments including one or more antimicrobial light sources, is configured to emit light sufficient to inactivate one or more microorganisms on a touch screen display surface. The lighting array may individually control activation of the one or more antimicrobial light segments based on user presence information, time of day information, and/or touch screen display usage information. A touch screen display assembly includes a housing, a touch screen display and a lighting array including one or more antimicrobial light segments.

32 Claims, 8 Drawing Sheets

(56) References Cited

U.S. PATENT DOCUMENTS

| | | | |
|---|---|---|---|
| 9,700,641 B2 | 7/2017 | Hawkins et al. | |
| 9,839,706 B2 | 12/2017 | Anderson et al. | |
| 9,963,597 B2 | 5/2018 | Aizenberg et al. | |
| 9,981,051 B2 | 5/2018 | Shur et al. | |
| 10,232,066 B2 | 3/2019 | Bailey | |
| 10,773,690 B2 | 9/2020 | Dellock et al. | |
| 11,229,716 B2 | 1/2022 | Vasilenko | |
| 2004/0175290 A1 | 9/2004 | Scheir et al. | |
| 2006/0021375 A1 | 2/2006 | Wetzel et al. | |
| 2010/0303671 A1 | 12/2010 | Bertrand | |
| 2011/0216042 A1 | 9/2011 | Wassvik et al. | |
| 2013/0224086 A1 | 8/2013 | Stibich et al. | |
| 2014/0061509 A1 | 3/2014 | Shur et al. | |
| 2014/0079587 A1 | 3/2014 | Dayton | |
| 2014/0300581 A1 | 10/2014 | Aurongzeb et al. | |
| 2015/0182647 A1 | 7/2015 | Ranta et al. | |
| 2016/0271803 A1 | 9/2016 | Stewart | |
| 2016/0375161 A1 | 12/2016 | Hawkins et al. | |
| 2017/0095585 A1 | 4/2017 | Smetona et al. | |
| 2017/0100989 A1 | 4/2017 | Chapaton et al. | |
| 2017/0246331 A1 | 8/2017 | Lloyd | |
| 2017/0333582 A1 | 11/2017 | Davis | |
| 2017/0368213 A1 | 12/2017 | Mintie et al. | |
| 2018/0023821 A1 | 1/2018 | Kim et al. | |
| 2018/0046166 A1 | 2/2018 | Kumar et al. | |
| 2018/0117189 A1 | 5/2018 | Yadav et al. | |
| 2018/0117190 A1 | 5/2018 | Bailey | |
| 2018/0117193 A1 | 5/2018 | Yadav et al. | |
| 2018/0124883 A1 | 5/2018 | Bailey | |
| 2018/0126021 A1 | 5/2018 | Valentine et al. | |
| 2018/0154027 A1 | 6/2018 | Anderson et al. | |
| 2018/0243452 A1 | 8/2018 | Hawkins et al. | |
| 2018/0243453 A1 | 8/2018 | Hawkins et al. | |
| 2018/0345485 A1 | 12/2018 | Sinnet et al. | |
| 2018/0360077 A1 | 12/2018 | Krebs et al. | |
| 2019/0001930 A1* | 1/2019 | Dellock | A61L 2/10 |
| 2019/0176338 A1 | 6/2019 | Zito et al. | |
| 2019/0298871 A1 | 10/2019 | Dobrinsky | |
| 2020/0205926 A1 | 7/2020 | Keibel | |
| 2020/0289683 A1 | 9/2020 | Christian et al. | |

FOREIGN PATENT DOCUMENTS

| | | | |
|---|---|---|---|
| CN | 104704067 A | 6/2015 | |
| CN | 104736261 A | 6/2015 | |
| CN | 105163605 B | 12/2015 | |
| CN | 204864170 U | 12/2015 | |
| CN | 105856259 A | 8/2016 | |
| CN | 105879148 A | 8/2016 | |
| CN | 105963730 A | 9/2016 | |
| CN | 20547250 A | 11/2016 | |
| CN | 106272467 A | 1/2017 | |
| CN | 206085069 U | 4/2017 | |
| CN | 206795846 U | 12/2017 | |
| CN | 108025182 A | 5/2018 | |
| CN | 108068125 A | 5/2018 | |
| CN | 207710799 U | 8/2018 | |
| CN | 108601376 A | 9/2018 | |
| CN | 108606754 A | 10/2018 | |
| CN | 108714884 A | 10/2018 | |
| CN | 109065186 A | 12/2018 | |
| CN | 106444564 B | 1/2019 | |
| CN | 109131234 A | 1/2019 | |
| CN | 109202939 A | 1/2019 | |
| CN | 109276728 A | 1/2019 | |
| CN | 109316612 A | 2/2019 | |
| CN | 10981707 A | 3/2019 | |
| CN | 109431810 A | 3/2019 | |
| CN | 109481708 A | 3/2019 | |
| DE | 102017209966 A1 | 12/2018 | |
| EP | 3355940 A2 | 8/2018 | |
| JP | 2013104872 A | 5/2013 | |
| JP | 2015167470 A | 9/2015 | |
| JP | 2018117586 A | 8/2018 | |
| KR | 1499359 B1 | 3/2015 | |
| KR | 1724447 B1 | 4/2017 | |
| KR | 20180010824 A | 1/2018 | |
| KR | 20190054955 A | 5/2019 | |
| WO | 2006124211 A1 | 11/2006 | |
| WO | WO-2014036080 A1 * | 3/2014 | A61L 2/10 |
| WO | 2015051024 A1 | 4/2015 | |
| WO | WO-2015051024 A1 * | 4/2015 | A61L 2/10 |
| WO | WO-2014036080 A9 * | 5/2015 | |
| WO | 2017062260 A2 | 4/2017 | |
| WO | 2018087171 A1 | 5/2018 | |
| WO | WO-2018122009 A1 * | 7/2018 | |

OTHER PUBLICATIONS

U.S. Appl. No. 17/325,440, filed May 20, 2021, by Hatch et al.
International Preliminary Report on Patentability from International Application No. PCT/US2020/040508, dated Jan. 13, 2022, 10 pp.
U.S. Appl. No. 17/101,449, filed Nov. 23, 2020, by Finison.
"Light Fixture Kills Bacteria Safely, Continuously," Science Daily, Jun. 26, 2015, 2 pp.
"Hubbell Lighting Secures Licensing Agreement with the University of Strathclyde High Intensity Narrow Spectrum Technology," Hubbell Lighting, May 4, 2018, 3 pp.
Lacombe et al., "Reduction of Bacterial Pathogens and Potential Surrogates on the Surface of Almonds Using High-Intensity 405-nanometer light," Journal of Food Protection, vol. 79, No. 11, Nov. 2016, pp. 840-845.
Gunther et al., "The Effects of 405-nm Visible Light on the Survival of Campylobacter on Chicken Skin and Stainless Steel," Foodborne Pathogens and Disease, vol. 13, No. 5, May 2016.
Kim et al., "Antibacterial Effect and Mechanism of High-Intensity 405 ± 5 nm Light Emitting Diode on Bacillus Cereus, Listeria Monocytogenes, and *Staphylococcus aureus* Under Refrigerated Condition," Journal of Photochemistry and Photobiology B: Biology, vol. 153, Dec. 2015, pp. 33-39.
Murdoch et al., "Inactivation of Campylobacter Jejuni by Exposure to High-Intensity 405-nm Visible Light," Foodborne Pathogens and Disease, vol. 7, No. 10, Oct. 2010, pp. 1211-1216.
Roh et al., "Blue Light-Emitting Diode Photoinactivation Inhibits Edwardsiellosis in Fancy Carp (*Cyprinus carpio*)," Aquaculture, vol. 483, Jan. 20, 2018, pp. 1-7.
Ramakrishnan et al., "Differential Sensitivity of Osteoblasts and Bacterial Pathogens to 405-nm Light Highlighting Potential for Decontamination Applications in Orthopedic Surgery," Journal of Biomedical Optics, vol. 9, No. 10, Oct. 2014, 7 pp.
McDonald et al., "405 nm Light Exposure of Osteoblasts and Inactivation of Bacterial Isolates from Arthroplasty Patients: Potential for New Disinfection Applications?", European Cells and Materials, vol. 25, Mar. 7, 2013, pp. 204-214.
MacLean et al., "Sporicidal Effects of High-Intensity 405 nm Visible Light on Endospore-Forming Bacteria," Photochemistry and Photobiology, vol. 89, No. 1, Jan./Feb. 2013, pp. 120-126.
Liang et al., "Blue Light Induced Free Radicals from Riboflavin on *E. coli* DNA Damage," Journal of Photochemistry and Photobiology B: Biology, vol. 119, Dec. 29, 2012, pp. 60-64.
Endarko et al., "High-Intensity 405 nm Light Inactivation of Listeria Monocytogenes," Photochemistry and Photobiology, vol. 88, No. 5, Sep.-Oct. 2012, pp. 1280-1286.
Murdoch et al., "Bactericidal Effects of 405nm Light Exposure Demonstrated by Inactivation of *Escherichia, Salmonella, Shigella, Listeria*, and *Mycobacterium* Species in Liquid Suspensions and on Exposed Surfaces," The Scientific World Journal, vol. 2012, Apr. 1, 2012, 8 pp.
MacLean et al., "High-Intensity Narrow-Spectrum Light Inactivation and Wavelength Sensitivity of *Staphylococcus aureus*," Federation of European Microbiological Societies, Jun. 16, 2008, pp. 227-232.
Kingsley et al., "Evaluation of 405-nm Monochromatic Light for Inactivation of Tulane Virus on Blueberry Surfaces," Journal of Applied Microbiology, vol. 124, No. 4, Apr. 2018, pp. 1017-1022.
"LG Electronics LP153HD3B Installation Guide," retrieved from manualzz.com/doc/4030343/lg-electronics-lp153hd3b-installation-guide on May 11, 2020.

(56) References Cited

OTHER PUBLICATIONS

International Search Report and Written Opinion of International Application No. PCT/US2020/022594, dated Jul. 13, 2020, 19 pp.
"Single Color Outdoor Weatherproof LED Flexible Lightstrip Part No. WFLS-x," https://d114hh0cykhyb0.cloudfront.net/pdfs/WFLS-x.pdf, Apr. 21, 2014, 2 pp.
"Wireless LED 4 Channel EZ Dimmer Controller with Channel Pairing," https://www.superbrightleds.comjmoreinfojrgb-led-controllers/wireless-4-channelrgb-led-dimmer-receiver/3372/7141/#tab/Reviews, Jul. 17, 2018, 7 pp.
Notification of Transmittal of International Search and Written Opinion for counterpart application No. PCT/US2020/040508 dated Oct. 19, 2020, 16 pp.
Response to Communication Pursuant to Rules 161(1) and 162 EPC dated February 10, 2022, from counterpart European Application No. 20745393.7, filed Aug. 10, 2022, 36 pp.
First Office Action and Search Report, and translation thereof, from counterpart Chinese Application No. 2020800518423 dated Jun. 6, 2023, 23 pp.

* cited by examiner

TOUCH SCREEN DISPLAY SURFACE SANITIZATION USING ANTIMICROBIAL LIGHT

This application claims the benefit of U.S. Provisional Application No. 62/870,267, titled, "TOUCH SCREEN DISPLAY SURFACE SANITIZATION USING ANTIMICROBIAL LIGHT," filed Jul. 3, 2019, the entire content of which is incorporated herein by reference.

TECHNICAL FIELD

The disclosure relates to systems and methods of reducing microbial growth on environmental surfaces.

BACKGROUND

Contamination of environmental surfaces poses a risk for transmission of pathogens and other microorganisms. Bacteria and other harmful microorganisms can survive for extended periods of time on environmental surfaces. Contamination of commonly touched surfaces, such as those that are touched by multiple customers, students, and/or employees in a retail, healthcare, school or restaurant environment, can therefore contribute to transmission of microorganisms from one person to another. The microorganisms can include pathogenic microorganisms, such as gram-positive and gram-negative bacteria, yeasts, fungi, viruses, and parasites. Various illness-causing pathogens include *Listeria monocytogenes*, enterohemorrhagic *Escherichia coli*, *Salmonella*, *Staphylococcus aureus*, and the like. At certain levels, the presence of microorganisms on frequently touched surfaces may cause everything from a consumer's perception of a lower quality product, regulatory investigations and sanctions, individual cases of pathogen-based illness, and may even lead to pathogen-based illness outbreaks.

SUMMARY

In general, the disclosure is directed to systems and/or methods of reducing microbial growth on environmental surfaces. In some examples, the environmental surfaces may include a touch screen display or computing device including a touch screen display, such as a point-of-sale (POS), kiosk, multi-user or interactive video wall, mobile device, smart phone, tablet computer, laptop computer, desktop monitor, and/or any other touch-based or interactive display. The touch screen displays may vary in size from the very small (e.g., the size of a mobile phone display or even smaller) to the very large (e.g., a large multi-user, interactive video wall). The systems and/or methods of the present disclosure may help reduce the frequency at which such touch screen displays need to be cleaned to keep the microbial growth below acceptable levels.

In one example, the disclosure is directed to a lighting array comprising a fixture, and one or more antimicrobial lighting segments mounted on the lighting fixture, each antimicrobial lighting segment including one or more elements, wherein each element emits light at a wavelength, irradiance, and direction sufficient to inactivate one or more microorganisms on a target area of a touch screen display surface.

The lighting array may control each antimicrobial light segment is controlled based on touch screen display surface usage information. The lighting array may deactivate at least some of the antimicrobial lighting segments when the touch screen display surface usage information is indicative of presence of a user. Each of the one or more antimicrobial lighting segments may be individually controllable by the lighting array such that each lighting segment may be activated at a first, high setting, a second, modified setting, or a third, deactivated setting independently of the other one or more antimicrobial lighting segments.

The system may further comprise a presence sensor that detects presence of a user near the touch screen display surface. The lighting array may further control the one or more antimicrobial lighting segments based on the time of day. The touch screen display surface may include a plurality of target zones, and wherein the one or more antimicrobial lighting segments are individually controllable to direct light at the wavelength and irradiance sufficient to inactivate one or more microorganisms within one or more of the target zones.

Each antimicrobial lighting segment may include a substrate and a plurality of light-emitting diode (LED) elements, and wherein each LED element emits light including wavelengths in a range of about 405±15 nanometers. The lighting array may further include one or more lighting elements that emit light having a wavelength range in the visible spectrum. The one or more microorganisms may include at least one of *Listeria monocytogenes*, enterohemorrhagic *Escherichia coli*, *Salmonella*, and *Staphylococcus aureus*.

Each antimicrobial lighting segment may include a substrate and a plurality of light-emitting diode (LED) elements, wherein one or more of the LED elements emit light within a first antimicrobial wavelength range of about 380-420 nanometers, and one or more of the LED elements emit light within a second antimicrobial wavelength range of about 200-280 nanometers. Each antimicrobial lighting segment may include a substrate and a plurality of light-emitting diode (LED) elements, wherein one or more of the LED elements emit light within a first antimicrobial wavelength range of about 380-420 nanometers and one or more of the LED elements emit light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm or ultraviolet C (UVC) light within a wavelength range of 200-280 nm.

In another example, the disclosure is directed to an antimicrobial lighting assembly comprising a frame assembly configured for mounting around at least a portion of the perimeter of a touch screen display surface; and one or more antimicrobial lighting segments mounted on the frame assembly, each antimicrobial lighting segment including one or more antimicrobial lighting elements, wherein each antimicrobial lighting element emits light at a wavelength, irradiance, and direction sufficient to inactivate one or more microorganisms on a target area of the touch screen display surface.

The frame assembly may be mounted around the entire perimeter of the touch screen display surface. The antimicrobial lighting assembly may further include a sensor that detects presence of a user near the touch screen display, and wherein power to the antimicrobial lighting segments is deactivated upon detection of presence of the user. Subsequent to detection of presence of a user near the touch screen display, the sensor may detect that the user is no longer present near the touch screen display, and power to the antimicrobial lighting segments may be deactivated.

The frame assembly may be configured to mount on a bezel of the touch screen display. The frame assembly may be configured for retrofittable mounting around the perimeter of a touch screen display surface.

Each antimicrobial lighting segment may include a substrate and a plurality of light-emitting diode (LED) elements, wherein one or more of the LED elements emit light within a first antimicrobial wavelength range of about 380-420 nanometers, and one or more of the LED elements emit light within a second antimicrobial wavelength range of about 200-280 nanometers. Each antimicrobial lighting segment may include a substrate and a plurality of light-emitting diode (LED) elements, wherein one or more of the LED elements emit light within a first antimicrobial wavelength range of about 380-420 nanometers and one or more of the LED elements emit light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm or ultraviolet C (UVC) light within a wavelength range of 200-280 nm.

In another example, the disclosure is directed to a touch screen display assembly comprising a touch screen display configured for interaction with one or more users; a housing configured to receive the touch screen display; an antimicrobial lighting assembly mounted within the housing and comprising one or more antimicrobial lighting segments, each antimicrobial lighting segment including one or more antimicrobial lighting elements, wherein each antimicrobial lighting element emits light at a wavelength, irradiance, and direction sufficient to inactivate one or more microorganisms on a target area of the touch screen display surface, each of the one or more antimicrobial lighting segment mounted along at least a portion of an edge of the touch screen display so as to emit antimicrobial light in a direction to inactivate microorganisms on a target area of the touch screen display surface.

The housing may comprise one of a kiosk, a touch screen display monitor housing, or a video wall rack. Each of the one or more antimicrobial lighting elements may have a beam angle in the range of 12° to 60°. A first subset of the at least one or more antimicrobial lighting elements may have a first beam angle and a second subset of the at least one or more antimicrobial lighting elements may have a second beam angle that is different than the first beam angle. Each antimicrobial lighting segments may include a stacked arrangement of antimicrobial lighting segments, such that a first stack of antimicrobial lighting segments is mounted on the bezel of the touch screen display surface and a second stack of antimicrobial lighting segments is mounted above the first stack of antimicrobial lighting segments.

The touch screen display assembly may further include a controller that receives one or more signals usable to determine status information concerning the touch screen display and controls the antimicrobial lighting segments based on the determined status information concerning the touch screen display. The controller may further receive one or more signals usable to determine presence of a user and controls the one or more antimicrobial lighting segments based on whether or not a user is present. The controller may further individually control each antimicrobial lighting segment based on the received status information concerning the touch screen display. The controller may further individually control each antimicrobial lighting segment to provide antimicrobial illumination to one or more target areas on the touch screen display surface based on the received status information concerning the touch screen display.

The controller may receive one or more signals usable to determine status information concerning the touch screen display and individually controls the one or more antimicrobial lighting segments to provide antimicrobial illumination to one or more high touch target areas on the touch screen display.

Each antimicrobial lighting segment may include a substrate and a plurality of light-emitting diode (LED) elements, wherein one or more of the LED elements emit light within a first antimicrobial wavelength range of about 380-420 nanometers, and one or more of the LED elements emit light within a second antimicrobial wavelength range of about 200-280 nanometers. Each antimicrobial lighting segment may include a substrate and a plurality of light-emitting diode (LED) elements, wherein one or more of the LED elements emit light within a first antimicrobial wavelength range of about 380-420 nanometers and one or more of the LED elements emit light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm or ultraviolet C (UVC) light within a wavelength range of 200-280 nm.

The details of one or more examples are set forth in the accompanying drawings and the description below. Other features and advantages will be apparent from the description and drawings, and from the claims.

DETAILED DESCRIPTION

Figure 1:
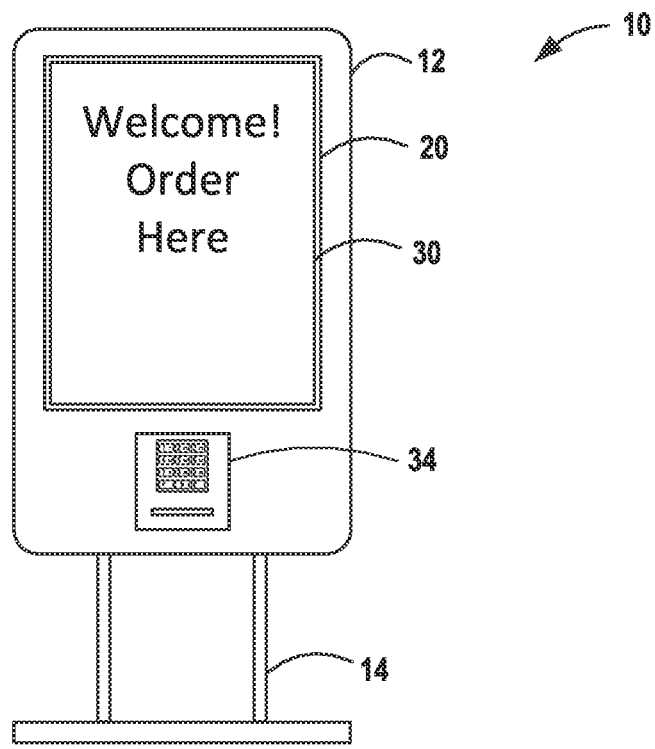
FIG. 1 is a diagram illustrating an example customer interface kiosk including an antimicrobial light array arranged for microbial inactivation on a touch screen surface in accordance with the present disclosure.

In general, the disclosure is directed to systems and/or methods of reducing microbial growth on environmental surfaces. In some examples, the environmental surfaces may include a touch screen display or computing device including a touch screen display, such as a point-of-sale (POS), kiosk, multi-user or interactive video wall, any type of customer-facing touch screen display surface, mobile device, smart phone, tablet computer, laptop computer, desktop monitor, and/or any other touch-based or interactive display. The touch screen displays may vary in size from the very small (e.g., the size of a mobile phone display or even smaller) to the very large (e.g., a large multi-user, interactive video wall). The systems and/or methods of the present disclosure may help reduce the frequency at which such touch screen displays needs to be cleaned to keep the microbial growth below acceptable levels.

Light having wavelengths in a range of approximately 405±10 nanometers (nm) has been demonstrated to decontaminate the air and exposed surfaces by inactivating microorganisms and pathogens. The systems and methods in accordance with the present disclosure concern the strategic application and control of an antimicrobial lighting system to touch screen display surfaces.

The antimicrobial light may include light within a first antimicrobial wavelength range of 380-420 nanometers (nm), and/or light within a second antimicrobial wavelength range, such as ultraviolet light within a wavelength range of 200-400 nanometers (nm). In some examples, the antimicrobial light within the first wavelength range has a peak wavelength of about 405 nm. In some examples, the antimicrobial light within the second wavelength range may include ultraviolet A (UVA) light within a wavelength range of 315-400 nm, ultraviolet B (UVB) light within a wavelength range of 280-315 nm, ultraviolet C (UVC) light within a wavelength range of 200-280 nm, and/or far ultraviolet C (far-UVC) light within a wavelength range of 200 to 222 nm.

Application of the antimicrobial light may improve hygiene and reduce growth of microorganisms on one or more surfaces of a touch screen display surface. In some examples, the systems and/or methods may complement manual cleaning procedures, such as spraying and/or wiping down, and help to maintain microbial growth below acceptable levels.

Light having wavelengths in a range of about 380-420 nm has been demonstrated to decontaminate the air and exposed surfaces by inactivating microorganisms and pathogens. For purposes of the present disclosure, in some examples, the term "antimicrobial light" includes light within a first wavelength range of about 380-420 nm. In some examples, the antimicrobial light within the first wavelength range has a peak wavelength of about 405 nm. The antimicrobial light has sufficient irradiance (power received by a target surface per unit area) of these wavelengths to result in inactivation of one or more microorganisms at the target surface within a desired period of time. In some examples, antimicrobial light source(s) may include one or more light source elements, such as light-emitting diodes (LEDs), that emit light within the first wavelength range of about 380-420 nm. In some examples, the antimicrobial light within the first wavelength range emitted by the LEDs has a peak wavelength of about 405 nm. It shall be understood that the particular range of wavelengths emitted by the light source element(s) may vary somewhat from these stated ranges, depending, for example, on the response curve for each particular light source element, and the disclosure is not limited in this respect. Also, each light source element does not necessarily emit light across the entire wavelength range. In general, the antimicrobial light contains at least some of these wavelengths at a sufficient intensity to inactivate one or more microorganisms on a target surface within a desired period of time.

In some other examples, the "antimicrobial light" may include light within a second wavelength range, wherein the second wavelength range includes ultraviolet light within a wavelength range of 200-400 nanometers (nm). The ultraviolet light may include ultraviolet A (UVA) light within a wavelength range of 315-400 nm, ultraviolet B (UVB) light within a wavelength range of 280-315 nm, ultraviolet C (UVC) light within a wavelength range of 200-280 nm, and/or far ultraviolet C (far-UVC) light within a wavelength range of 200 to 222 nm. The intensity of the ultraviolet light has sufficient irradiance (power received by a target surface per unit area) of these wavelengths to result in inactivation of one or more microorganisms at the target surface within a desired period of time. In some examples, the light source elements that emit light within the second antimicrobial wavelength range include light-emitting diodes (LEDs). The light of the first wavelength range and the light of the second wavelength range may be emitted by the same light source elements or by different light source elements.

The spectral energy of the combined antimicrobial light (that is, the light of the first wavelength range combined with the light of the second wavelength range) may be designed such that the proportion of spectral energy of light in the first wavelength range and the proportion of spectral energy within the second wavelength range is optimized with respect to the type of microorganisms targeted, the amount of time required to sufficiently inactivate the targeted microorganisms, to minimize damage or other degradation of the target surfaces, to minimize human exposure to certain wavelengths of antimicrobial light, and/or other factors which may influence the relative amount of the antimicrobial wavelengths to be applied. For example, in some applications, the combined light may be designed such that at least 30% of the spectral energy of the combined light is within the first wavelength range and at least 30% of the spectral energy of the combined light is within the second wavelength range.

Light elements within the second antimicrobial wavelength range can include light elements that emit one or more of UVA, UVB and/or UVC wavelengths, and these may be used in conjunction with or independently of light elements that emit light within the first antimicrobial wavelength range of 380-420 nm. The light elements of the second antimicrobial wavelength range may be interspersed throughout the array can be activated in such manner that they are cycled sequentially, pulsed independent of the light elements of the first antimicrobial wavelength range, operated at different power settings, etc.

For combined light (that is, the light of the first wavelength range combined with the light of the second wavelength range and the light of the third wavelength range), the proportion of spectral energy of light in the first wavelength range may be such that at least 30% of the spectral energy of the combined light is within the first wavelength range and at least 30% of the spectral energy of the combined light is within the second wavelength range.

In some examples, the antimicrobial light(s) may also include light of other wavelengths, such as visible light including wavelengths from about 380 to 740 nm. The intensity of the visible light may be sufficient for illumination when viewed by the human eye. The visible light and the antimicrobial light may be emitted from the same light source elements or from different light source elements.

An antimicrobial lighting system may include an array of one or more individually controllable antimicrobial light segments. Each antimicrobial light segment may include a substrate and one or more light emitting elements, wherein each of the light emitting elements emits light at a wavelength and irradiance sufficient to inactivate one or more microorganisms on a target surface. For example, an antimicrobial light segment may include an LED light strip including a flexible circuit board or strip populated with multiple surface-mounted LEDs. In other examples, an antimicrobial light segment may include a grid of LEDs printed on a circuit board, panel, or other solid substrate. The substrate may be rigid or flexible, depending upon the needs of the installation. Other examples may include LED tube lights, light bars, rope lights, bulbs, individual light emitting elements, and any other flexible or inflexible light element configuration or shape. The light segments may be customized in size and shape to both fit within the desired spaces within or on a touch screen display surface and to direct light at the wavelength(s) and irradiance at one or more target surfaces within or on the touch screen display to achieve a desired level of microbial inactivation at those surfaces, or to reduce or prevent microbial growth at those surfaces, within a desired period of time.

Each individual light element may be directional or omnidirectional. In addition, not all light elements need to have the same directionality; that is, "flood" and "spot" style light elements may be used in the same light segments or through light segments of a lighting array. Individual control of the antimicrobial light segments, or of individual or groups of antimicrobial light source elements within each light segment, may be based on the cycle and/or usage information regarding the touch screen display in which in which the antimicrobial light segments are installed, the room or environment in which the touch screen display is installed, the type(s) of microorganism(s) to be decontaminated, an amount of time expected to be available for decontamination or an amount of time within which decontamination is desired to occur, the distance between the light source elements and the target surfaces, the time between decontamination events, the amount of soil residue on the target surface(s) and/or other factors that may affect the type and/or amount of antimicrobial light needed to adequately decontaminate the target surfaces within or on the touch screen display.

In one example, an antimicrobial lighting system may include an array of one or more individually controllable antimicrobial light segments positioned to provide antimicrobial illumination across a target surface, such as a touch screen display surface. The light array may be connected to receive usage data regarding the touch screen display, and may be controlled based on the received usage data. For example, a motion sensor may detect presence of a user at or near the touch screen display, and the light array may enable or disable one or more of the antimicrobial light segments based on the user presence information. In another example, the light array may enable or disable one or more of the antimicrobial light segments based on time of day information.

The touch screen display may comprise a single target area that includes the entire touch screen display surface, or the touch screen display surface may be divided into multiple target areas or zones. Each identified target area on the touch screen display surface is illuminated with light of an antimicrobial wavelength at a sufficient dosage to effect microbial inactivation on identified target surfaces or zones within the touch screen display surface. The dosage may be defined as the irradiance, or the energy received by a surface per unit area (e.g., as measured in Joules per square centimeter, $J \cdot cm^{-2}$, $W \cdot s \cdot cm^{-2}$) of the antimicrobial wavelength(s) measured at the target surface. The irradiance is dependent at least in part by the power applied to the light source(s), the distance from the light source to the surface, the total surface area illuminated, and the time of exposure.

In some examples, it is not necessary to continuously illuminate all zones or surfaces on the touch screen display, nor is it necessary to illuminate all zones or surfaces at the same time or at the same dose. Zones can be treated automatically and selectively by the antimicrobial light when, for example, the treatment is determined to be most effective, based on the received usage information or on the time of day information. In other words, for example, when the usage information indicates presence of a user, the light array may disable one or more antimicrobial lighting segments so that the user is not exposed to potentially harmful wavelengths or so that the antimicrobial light does not affect the user experience of the touch screen display. When the usage information indicates that no user is present, the light array may enable the antimicrobial lighting segments so as to achieve some microbial inactivation at the touch screen surface when no one is using the touch screen.

The antimicrobial light treatment protocol may include a high exposure setting (full power on or highest intensity) antimicrobial cycle mode that occurs when usage of the machine is predicted to be in an unused state (at night, or during closing times, for example) as well as a treatment interrupt mode (power down) for power savings or to minimize exposure risk (for example, when a touch screen display or other equipment associated with the touch screen display is being serviced). The antimicrobial light treatment protocol may also include a reduced power mode or modified setting in which certain antimicrobial light segments are selectively controlled to output a reduced intensity, but at a level that is sufficient to inactivate one or more microorganisms at the target surface(s). For example, the antimicrobial light elements could be cycled in a "race" mode such that light elements will cycle sequentially throughout the array.

The antimicrobial lighting systems may include lighting segments and/or lighting elements that output light within one or more antimicrobial wavelength range(s). For example, some lighting segments or lighting elements may output light within a first antimicrobial wavelength range and some lighting segments or lighting elements may output light within a second antimicrobial wavelength range.

In another example, when the touch screen is experiencing high frequency of use the antimicrobial lighting system may switch to a high power (high intensity or high sanitizing) mode between users. For example, in a self-service restaurant environment during high usage times, the antimicrobial light treatment may be put into a high sanitizing mode between customers, so as to apply high intensity or highly sanitizing antimicrobial light as often as possible when the touch screen is experiencing increased usage levels, and when the risk for cross-contamination between users is increased.

The antimicrobial lighting systems may include lighting segments and/or lighting elements that output light at antimicrobial wavelengths alone or in combination with light of other wavelengths (e.g., one or more wavelengths of visible light). For example, some lighting segments or lighting elements may output antimicrobial light (such as light within the first antimicrobial wavelength range and/or light within the second antimicrobial wavelength range) while other lighting segments or lighting elements output light within the visible spectrum. This may help provide illumination within or on the touch screen display surface that is aesthetically pleasing to humans and/or to more closely represent true colors than illumination by antimicrobial wavelengths alone, which may appear blue to the human eye.

An antimicrobial light array may be installed and configured with respect to the touch screen display surface such that there is overlapping illumination from each successive lighting element at the target surface at which microbial inactivation is desired. This cone of illumination illuminates a surface area dependent upon the design and physical arrangement of the individual light elements in each lighting segment and the distance of the element(s) from the target surface. The design and installation of the light array will be such that there is continuous or intermittent illumination at the surface throughout the target surface being treated. It shall be understood that the irradiance power at the surface being treated is dependent upon the distance between the emitter and the surface. The power of the antimicrobial light is controlled such that sufficient irradiance required for microbiological mitigation within the desired time period is achieved. It shall further be understood that the time/irradiance/distance power relationship required for microbiological mitigation depends upon the target organism(s).

LED lifetime of the antimicrobial lights can range from hundreds to in excess of 100,000 hours of operation. Furthermore, the emitted power of the lamp can be modulated using a Pulse-Width-Modulation (PWM) technique to achieve higher irradiant power without stressing the antimicrobial light to the extent that the light's lifetime is adversely affected when operated under constant power. The frequency and duty cycle applied to the antimicrobial light segments may be modulated to achieve the desired irradiance power at the target surface(s). PWM enables the color temperature (spectral distribution) of the LED lamp to be maintained while varying the observed lamp brightness.

In some examples, antimicrobial light segments may be fabricated from, for example, flexible LED light strips in which each LED light element is designed to emit wavelengths in the first antimicrobial wavelength range of about 380-420 nm and having a peak wavelength of about 405 nm or in a second antimicrobial wavelength range of about 200-280 nm. Such antimicrobial light segments may be configured and arranged to treat the touch screen display surface. The antimicrobial light segments may also be configured and arranged to treat areas around or associated with the touch screen display surface, such as the front panel or bezel around the touch screen display surface, other user interaction surfaces such a payment or credit card swipe surfaces, touch pads, key pads, stylus, keyboards, printers, etc.

Target organisms that may be found on touch screen display surfaces, and that may be inactivated using the antimicrobial lighting systems and methods of the present disclosure include, but are not limited to, bacteria, yeasts, and molds, such as *Bacillus* species, *Pseudomonas* species, *Listeria monocytogenes, Staphylococcus aureus, Salmonella* species, *E. coli*, coliforms, *Legionella* species, *Acinetobacter* species, *Candida* species, *Saccharomyces* species, *Aspergillus* species, *Alcaligenes, Flavobacterium*, and any other pathogen or microorganism that may be encountered in such environments.

FIG. 1 is a diagram showing an example touch screen kiosk 10 including a frame or case 12, a stand 14, a touch screen display 30, and an antimicrobial light array 20 arranged for microbial inactivation of touch screen display surface 30 in accordance with the present disclosure. In this example, kiosk 10 also includes a payment terminal 34 having a keypad, credit/debit card swipe slot, etc. Kiosk 10 also includes or is connected for electronic communication with one or more computing device(s) that controls the information displayed on touch screen display 30 and that receives and analyzes touch inputs received at touch screen display 30. In this way, kiosk 10 may be used in many different ways and in many different industries, such as allowing users to place self-service orders at restaurants, check-in for a doctor's appointment, check-in for a flight at the airport, park their car, and to facilitate many other tasks.

In some examples, it may be desirable to provide substantially evenly distributed antimicrobial illumination across the entire surface area of the touch screen display. In other examples, it may be desirable to provide relatively higher intensity antimicrobial illumination at certain areas or zones within the surface area of the touch screen display, such as those areas or zones on the touch screen display surface that are more frequently touched by users, whereas other less frequently touched areas or zones within the surface area of the touch screen display surface may be provided with relatively lower intensity antimicrobial illumination. It shall be understood, therefore, that the pattern of antimicrobial illumination across the surface area of the touch screen display surface may vary depending upon the application and/or the environment in which the touch screen display is to be used, and that the disclosure is not limited in this respect.

Figure 2:
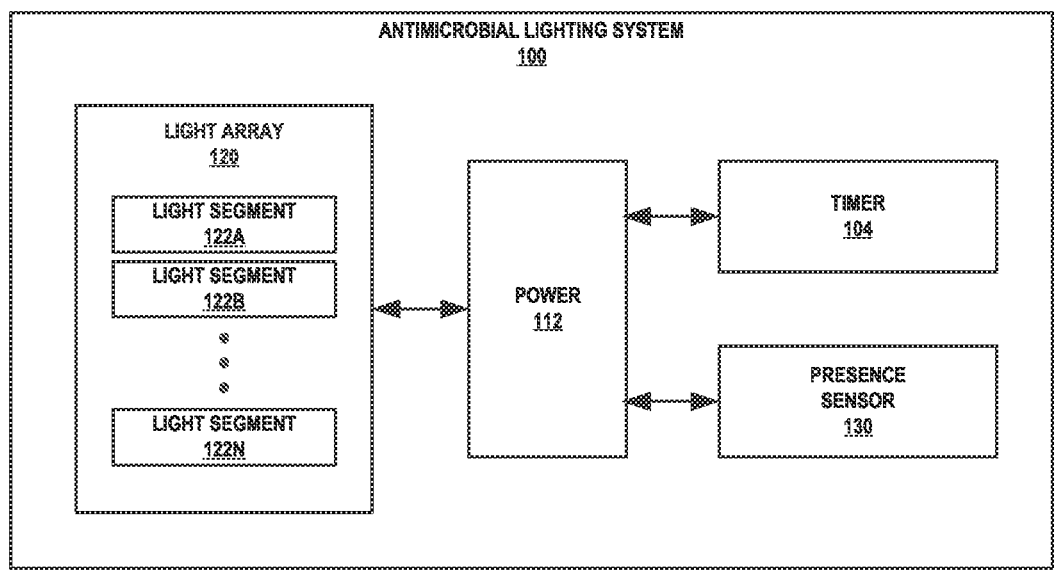
FIG. 2 is a block diagram illustrating an example antimicrobial lighting system including a light array and one or more individually controllable antimicrobial light segments in accordance with the present disclosure.

FIG. 2 is a block diagram illustrating an example antimicrobial lighting system 100. Antimicrobial lighting system 100 includes a light array 120 including one or more individually controllable antimicrobial light segments 122A-122N. Antimicrobial lighting system 100 also includes a power module 112, a timer 104 and a presence sensor 130. A Power module 112 is configured to provide power to the light array 120. Timer 104 provides time of day information to the power module 112. Presence sensor 130 detects presence of a user at the touch screen display. User presence may be associated with usage of the associated touch screen display. In this example system, power to the light array may be controlled based on time of day, based on detected presence (or absence) of a user, or may be based on actual usage of the touch screen display. For example, light array 120 may be controlled based on presence information received from presence sensor 130. For example, presence sensor 130, such as a motion sensor, may detect presence of a user at or near the touch screen display, and the light array 120 may enable or disable one or more of the antimicrobial light segments 122A-122N based on this detected user presence information. In another example, timer 104 may provide time of day information and light array 120 may enable or disable one or more of the antimicrobial light segments 122A-122N based on time of day information. In another example, antimicrobial lighting system 100 may receive actual touch screen usage information (e.g., one or more indications of detected touch screen usage generated based on receipt of touch screen inputs) from a controller associated with the touch screen display, and light array 120 may enable or disable one or more of the antimicrobial light segments 122A-122N based on receipt of actual touch screen usage information.

Antimicrobial lighting system 100 may also control light array 120 such that the entire touch screen display surface comprises a single target area, or the touch screen display surface may be divided into multiple target areas or zones. Light array 120 is controlled such that each identified target area on the touch screen display surface is illuminated with light of an antimicrobial wavelength at a sufficient dosage to effect microbial inactivation on identified target surfaces or zones within the touch screen display surface. The dosage may be defined as the irradiance, or the energy received by a surface per unit area (e.g., as measured in Joules per square centimeter, $J \cdot cm^{-2}$, $W \cdot s \cdot cm^{-2}$) of the antimicrobial wavelength(s) measured at the target surface. The irradiance is dependent at least in part by the power applied to the light source(s), the distance from the light source to the target area on the touch screen display surface, the total surface area illuminated, and the time of exposure.

In some examples, it is not necessary to continuously illuminate all zones or surfaces on the touch screen display, nor is it necessary to illuminate all zones or surfaces at the same time or at the same dose. Zones can be treated automatically and selectively by the antimicrobial light when, for example, the treatment is determined to be most effective, based on received user presence information, usage information, time of day information, or on a periodic basis. In other words, for example, when the user presence information or touch screen usage information indicates usage of the touch screen display, the light array may disable one or more antimicrobial lighting segments so that the user is not exposed to potentially harmful wavelengths, and/or, so that activation of the antimicrobial light does not affect the user experience of the touch screen display. When the user presence or usage information indicates that no user is present or the touch screen is not being used, the light array may enable one or more of the antimicrobial lighting segments so as to achieve some microbial inactivation at the touch screen surface.

The antimicrobial light treatment protocol may include a high exposure setting (full power on or highest intensity) antimicrobial cycle mode that occurs when usage of the machine is predicted to be in an unused state (at night, or during closing times, for example) as well as a treatment interrupt mode (power down) for power savings or to minimize exposure risk (for example, when a touch screen display or other equipment associated with the touch screen display is being used or serviced). The antimicrobial light treatment protocol may also include a reduced power mode or modified setting in which certain antimicrobial light segments are selectively controlled to output a reduced intensity, but at a level that is sufficient to inactivate one or more microorganisms at the target surface(s). The individual light segments 122A-122B may thus be individually and selectively controlled to provide antimicrobial illumination at one or more intensity settings and at various times throughout the day to ensure sufficient antimicrobial inactivation at the target surfaces while ensuring a safe and pleasing experience for the user.

Control of the settings may be determined based on the time of day. For example, lighting array 120 may be controlled based on time and date information from timer 104 to determine whether the current time corresponds to a heavy usage time of the touch screen display or to a reduced or standby usage time of the touch screen display. In a restaurant application, for example, a heavy usage time for a touch screen display may correspond to the hours around mealtimes, such as breakfast, lunch, and/or dinner, while a reduced usage time may correspond to nighttime hours or other times when the restaurant is closed. Light array 120 may therefore determine the time and date from information received from timer 104 and individually control activation of selected antimicrobial light segments 122A-122N based on the time and date. For example, light array 120 may activate all antimicrobial light segments 122A-122N at a maximum setting upon determining that the time and date correspond to a time when the touch screen display typically experiences a reduced or no usage level (such as when a restaurant is closed). Array control module 108 may activate selected antimicrobial light segments 122A-122N at a reduced setting (e.g., a lower power or off setting) upon determining that the time and date correspond to a time when the touch screen display typically experiences relatively higher usage levels and/or maximum usage levels.

In some examples, antimicrobial lighting system 100 is a standalone system that may be retrofitted onto an existing case or housing of a touch screen display. For example, an antimicrobial lighting system 100 packaged in a rectangular frame and having dimensions corresponding to touch screen display 30 of the kiosk 10 of FIG. 1 may be retrofitted onto an existing case 12 or housing of kiosk 10 to provide antimicrobial illumination of the touch screen display surface 30. Alternatively, antimicrobial lighting system 100 may be integrated into the manufacture of the touch screen display. For example, an antimicrobial lighting system 100 may be integrated into the case or housing 12 of kiosk 10 to provide antimicrobial illumination of the touch screen display surface 30. In such an example, antimicrobial lighting system 100 may share one or more electronic components with the computing device of kiosk 10, such as the controller, storage devices, power supply, etc. In this way, the control modules for selectively and individually controlling activation/deactivation of the one or more light segments 122A-122N of light array 120 may be stored in and executed by the kiosk control circuitry and/or computing device components.

It shall be understood that antimicrobial light arrays including one or more antimicrobial light segments may be adapted for antimicrobial illumination of any touch screen display surface. For example, the antimicrobial light segments 122A-122N may be straight line segments, flexible LED light strips, curved light segments, or may be bent or curved to fit almost any shape of touch screen display.

Each light segment 122A-122N includes one or more individual antimicrobial light sources. For example, one or more of antimicrobial light segments 122A-122N may be implemented using a commercially available LED light strip having a peak wavelength of about 405±5 nm, such as the Single Color Outdoor Weatherproof LED Flexible Light Strip, wavelength 405 nm, Part Number WFLS-UV30, available from Super Bright LEDs Inc., of St. Louis, Mo., USA (www.superbrightleds.com).

Each antimicrobial light segment 122A-122N may be individually controllable such that they may be activated and/or deactivated independently of one another. Each of the antimicrobial light segments 122A-122N, either alone or in combination with one or more of the other antimicrobial light segments 122A-122N, emits antimicrobial light at a wavelength and irradiance sufficient to inactivate one or more microorganisms on the target area of the touch screen display surface(s). For example, one or more of antimicrobial light segments 122A-122N may include one or more light source elements that emit antimicrobial light within a first wavelength range of 380-420 nm and having an irradiance sufficient to inactivate one or more microorganisms at the target surface(s) within a specified period of time. In some examples, the light within the first wavelength range has a peak wavelength of about 405 nm. As another example, one or more of antimicrobial light segments 122A-122N may include one or more light source elements that emit antimicrobial light within a second wavelength range, wherein the second wavelength range may include ultraviolet A (UVA) light within a wavelength range of 315-400 nm, ultraviolet B (UVB) light within a wavelength range of 280-315 nm, ultraviolet C (UVC) light within a wavelength range of 200-280 nm, and/or far ultraviolet C (far-UVC) light within a wavelength range of 200 to 222 nm and having an irradiance sufficient to inactivate one or more microorganisms at the target surface(s) within a specified period of time. Use of multiple customizable and individually controllable antimicrobial light segments allows for controlled distribution and illumination of antimicrobial light to achieve microbial inactivation across the entire surface of a touch screen display surface.

Figure 3:
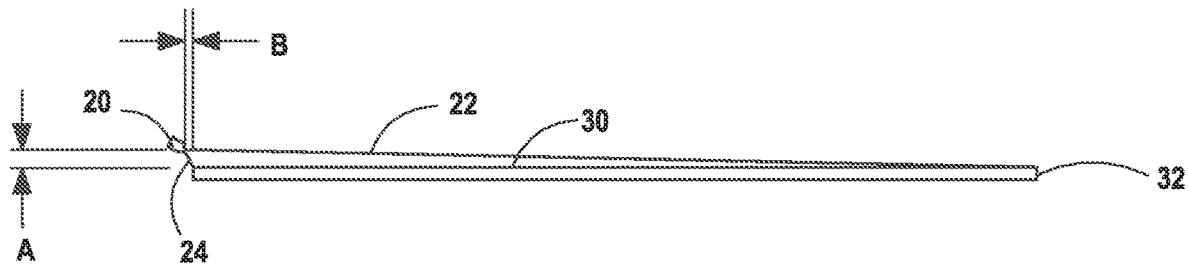
FIG. 3 is a cross-sectional side view of an example arrangement of an antimicrobial light source and a touch screen surface in accordance with the present disclosure.

FIG. 3 is a cross-sectional side view of an example arrangement including an antimicrobial light source 20 and a touch screen surface 30 in accordance with the present disclosure. In general, the light source 20 is arranged to direct antimicrobial light across the target surface, in this example, the entire width of the touch screen display surface 30, to mitigate microbiological activity on the surface. Light source 20 is mounted in a light fixture or frame such that light source 20 irradiates the entire width of the touch surface 30 with antimicrobial light. For example, an LED with a 60° beam angle can be mounted at a fixed distance, indicated by reference "B," and elevation, indicated by reference "A," at a specific angle, indicated by reference "C," from the touch surface 30 having a width of 16.75 inches in this example. However, it shall be understood that touch screen display surfaces of any size and shape are to be considered within the spirit and scope of the present disclosure.

Rays 22, 24 emanating from antimicrobial light source 20 indicates irradiance with a 60° spread. The light source in this example is located 0.177 inches to the left (as indicated by reference "B") and 0.321 inches above the left edge of the touch surface (as indicated by reference "A"). The lamp is oriented at an angle of −31.1° relative to the plane of the touch surface (as indicated by reference "C"). At this angle the beam angle illuminates the entire width of the touch surface 30. The placement of the light source 20 depends upon the beam angle and width of the surface to be treated with the antimicrobial light.

Figure 4:
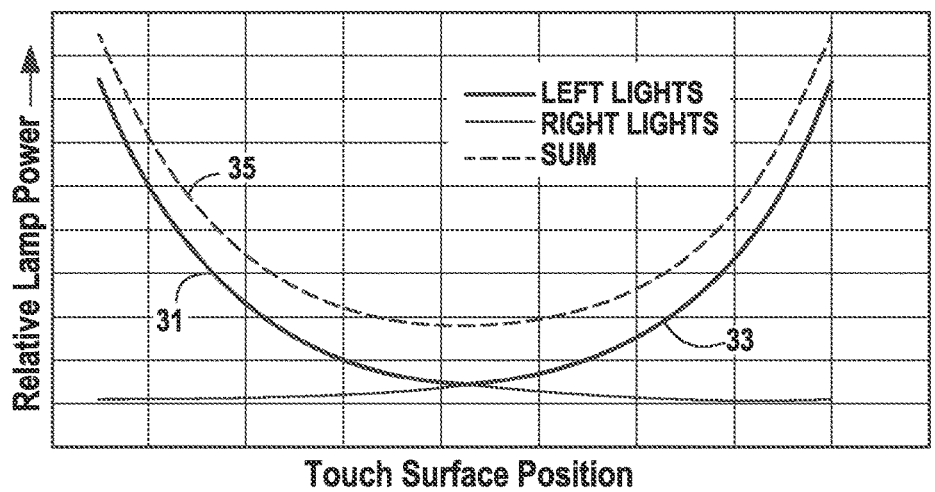
FIG. 4 is a graph showing the relationship of light intensity along the touch surface for the example antimicrobial light source arrangement of FIG. 3.

In one example, light segments including one or more light sources such as shown in FIG. 3 may be installed along at least two sides of the touch surface, left and right, for example. Due to the inverse-square relationship of light intensity decreasing with distance along the touch surface, it may be theorized that the center-most section of the touch surface will receive a lower antimicrobial light intensity. FIG. 4 is a graph showing the theoretical light intensity along the touch screen display surface 30 for such an example antimicrobial light source arrangement. The graph assumes two light sources, one on each side of the touch screen display surface (only one source 20 is shown in FIG. 3 for simplicity of illustration). As shown in FIG. 4, the theoretical intensity of the so-called left and right light sources, indicated by reference numerals 31 and 33, respectively, is highest at the edges nearest the light sources and drops off toward the center of the touch screen display surface. The combined intensity, indicated by reference numeral 35, is somewhat higher than the individual theoretical intensity of the individual light sources.

In other examples, assuming a 4-sided rectangular display shape, one or more antimicrobial light segments may be installed on all four sides of the touch screen display surface or on three sides of the touch screen display surface. In some examples, the one or more lighting segments may extend along at least one edge from one side to an opposite side of the touch screen display surface. In other examples, the one or more lighting segments may extend partially along one or more edges of the touch screen display surface.

In some examples, the intensities of the lamps should be sufficient to provide antimicrobial efficacy in the region of lowest lamp power over a pre-determined time period.

Figure 5:
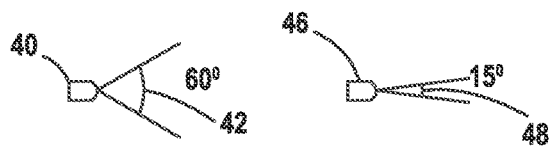
FIG. 5 is a diagram illustrating two example antimicrobial light sources having different beam angles.

In another example, a second light source may be incorporated within the lighting fixture(s). In this example, the second light source has a narrower beam angle than the first light source, as shown in FIG. 5. FIG. 5 is a diagram illustrating two example antimicrobial light sources 40 and 46 having different beam angles. A first antimicrobial light source 40 has a beam angle (indicated by reference numeral 42) of 60°. A second antimicrobial light source 46 has a beam angle (indicated by reference numeral 48) of 15°.

Figure 6:
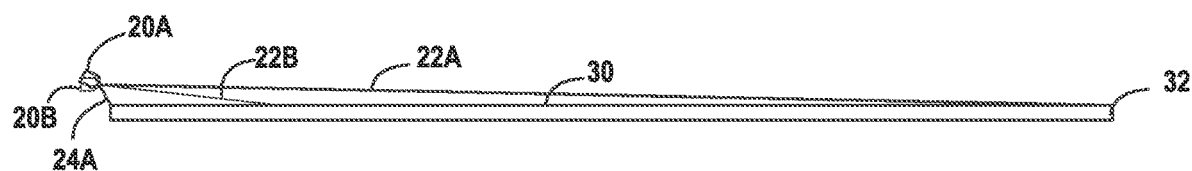
FIG. 6 is a cross-sectional side view of another example arrangement of antimicrobial light sources and a touch screen surface in accordance with the present disclosure.
Figure 7:
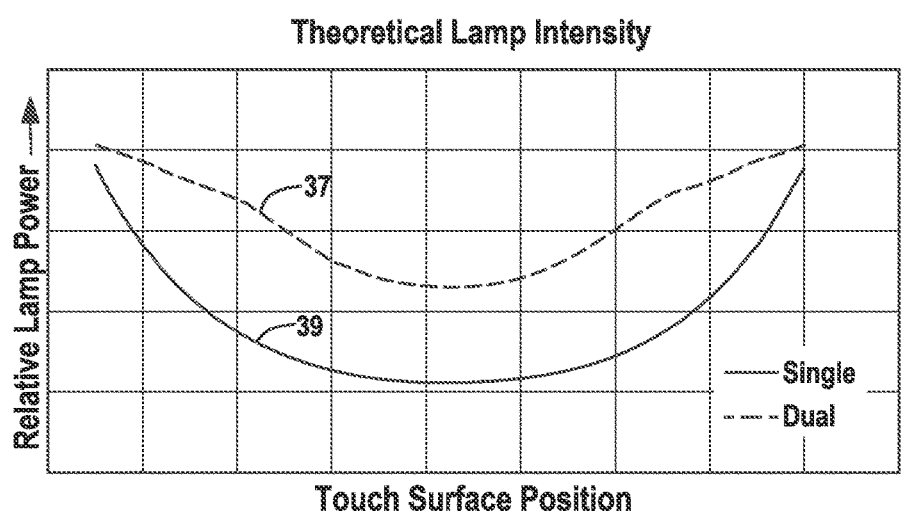
FIG. 7 is a graph showing the relationship of light intensity along the touch surface for the example antimicrobial light source arrangement of FIG. 5.

FIG. 6 is a cross-sectional side view of another example arrangement of two antimicrobial light sources 20A and 20B and a touch screen display surface 30 in accordance with the present disclosure. The two light sources are shown on one side in FIG. 6 for simplicity of illustration. Incorporating the second lamp where the energy is centered along the centermost section of the touch surface could increase the antimicrobial efficacy. This design increases the energy impinging upon the centermost area of the touch surface. FIG. 7 is a graph showing the theoretical relationship of light intensity along the touch screen display surface 30 for the example antimicrobial light source arrangement of FIG. 6, as indicated by reference numeral 37, compared to that of a single light source, as indicated by reference numeral 39. The model shows a significant increase in the antimicrobial light impinging on the centermost section of the touch surface, as indicated by reference numeral 37. Further design improvements could conceivably provide a nearly constant antimicrobial light power across the surface.

Figure 8:
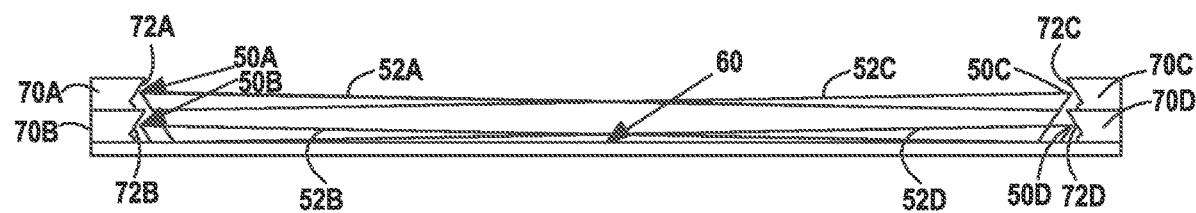
FIG. 8 is a cross-sectional side view of another example arrangement of antimicrobial light sources and a touch screen surface in accordance with the present disclosure.

FIG. 8 is a cross-sectional side view of another example arrangement of antimicrobial light sources 50A-50D and a touch screen display surface 60 in accordance with the present disclosure. In this example, a fixture 70 includes antimicrobial light sources 50A-50D in a stacked arrangement to add lights and change the illumination angles for at least one set of light sources. Fixture 70 includes mounting surfaces 72A-72D for each of light sources 50A-50D, respectively. Each light source 50A-50D has a corresponding beam width indicated by reference numerals 52A-52D, respectively. The angle of the mounting surfaces 72A-72D and the beam widths 52A-52D may be adjusted such that substantially even antimicrobial illumination across the entire width of the touch screen display surface 60.

EXAMPLES

A surrogate touch surface was prepared from a sheet of acrylic plastic measuring 17-inches wide. Stacked antimicrobial light fixtures were affixed to the surface as shown in FIG. 8. The lights were Superbright LEDs model WFLS-X3. The operating voltage of these LEDs is 9-14.8 VDC; however, in the experiment the LEDs were driven at 24 VDC via pulse-width-modulation (PWM) at a frequency of 660 Hz and a 20% duty cycle. This was done to increase the kill efficacy by increasing the energy emitted by the lamps.

Figures 9, 10:
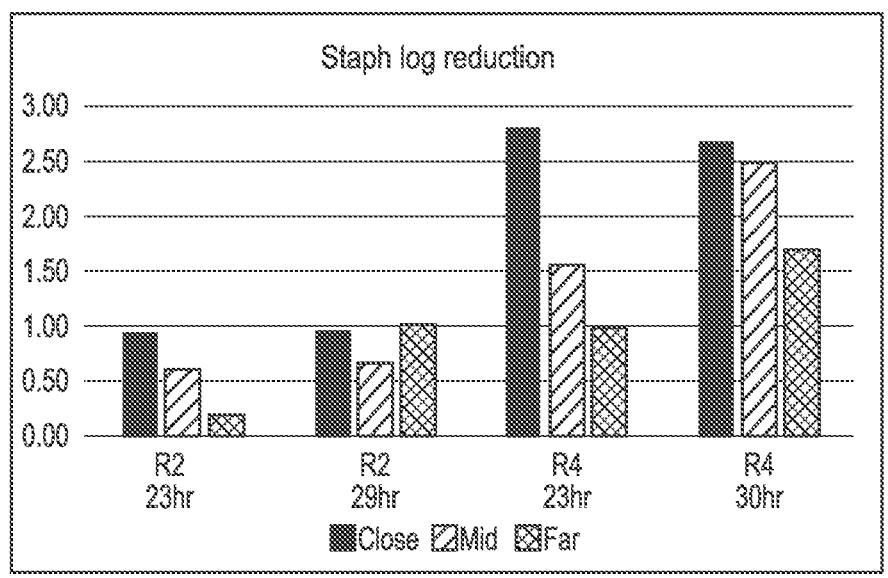
FIG. 9 is a diagram showing the physical layout of a designed experiment using the light arrays of FIG. 8 and showing three test locations on a test surface relative to the locations of the light arrays.
FIG. 10 is a graph showing the results of two experiments performed to determine the reduction of the pathogen *S. aureus* using the test apparatus shown in FIGS. 8 and 9.

The physical layout of the test surface is shown in FIG. 9, which illustrates the three test locations (close, mid, and far) relative to the light bars which were located at columns 1 and 17.

The sample surface was inoculated with the test organism following standard laboratory practices:

Each section was inoculated with 20 µl of culture and spread to within ⅛" of the edge of the section.

The acrylic panel was placed into an incubator (35 C) for drying. The panel will be in the chamber for 20-40 minutes or until visibly dry.

The panel was set up in the test location and the lights turned on.

Sections was swabbed after appropriate intervals such as 4, 6 and 24 h.

10 ml of Letheen broth will be added to a 3M speci-sponge in its collection bag to allow for the sponge to be moistened.

A section of the panel was sampled by moving the sponge horizontally three times followed by three vertical movements.

The sponge was then placed back into any remaining Letheen broth in the bag and stomached for 30 s. Liquid was squeezed from the sponge and processed.

Appropriate ten-fold dilutions were prepared from the collected samples using PBDW. A single 0.1 mL aliquot of the dilution was spread plated using Tryptic Soy Agar.

A control section of the acrylic panel was concurrently processed following the same procedure without exposure to the light source.

The test was conducted in triplicate for each organism at each time point.

Two separate tests were performed with the apparatus:

R2. Single light fixture on each side of the test surface powered at 12VDC.

R4. Stacked light fixtures on each side of the test surface powered via PWM at 24VDC.

The results of the test for *S. aureus* are shown in the chart of FIG. 10. The test results for test R2 show minimal microbial reduction on the test surface over the 29 hour period. Test R4, with the increased lamp number and power, shows improved microbial kill at all locations. It is recognized that higher energy is required to increase microbiological reduction, especially at the location furthest from the lamps.

Figure 11:
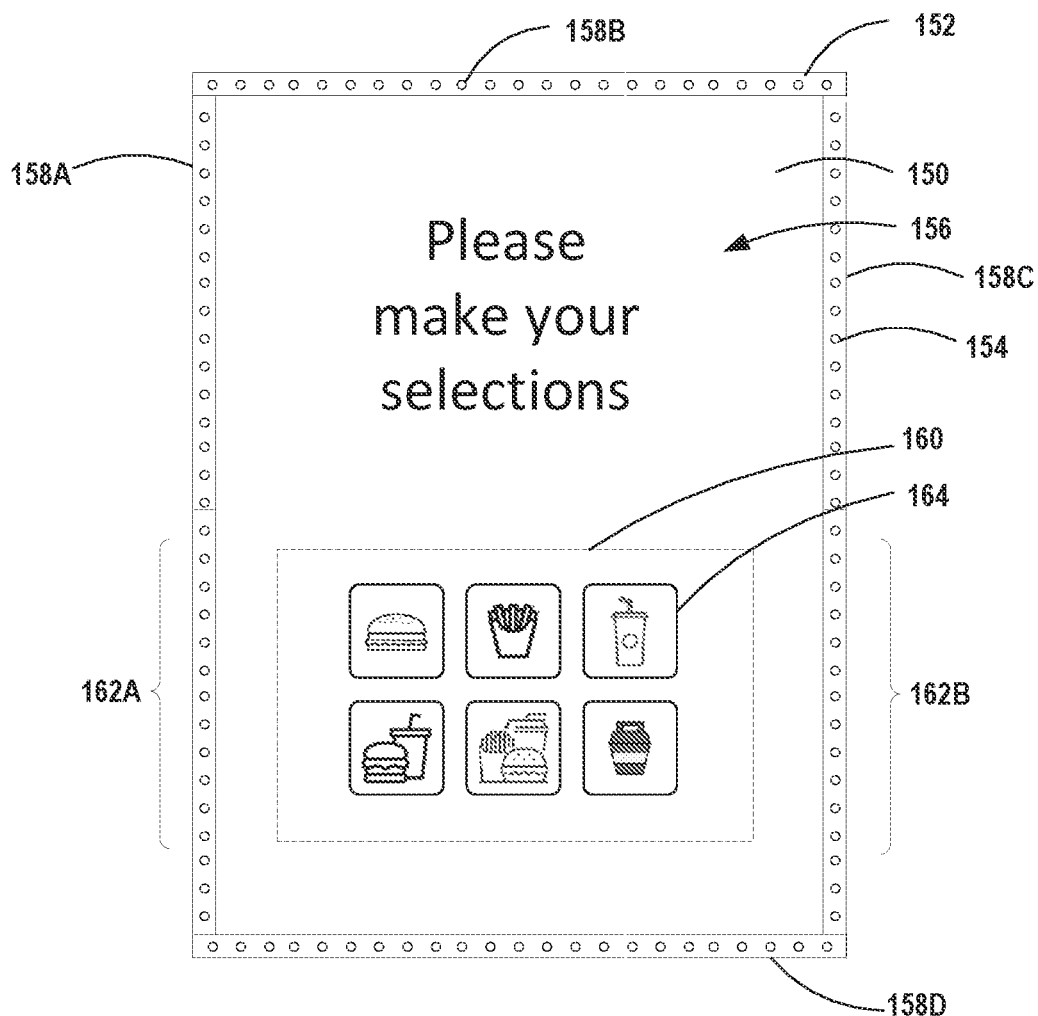
FIG. 11 shows an example touch screen display assembly having one or more antimicrobial lighting segments extending around the perimeter of touch screen display surface.

FIG. 11 shows an example touch screen display assembly 152 having one or more antimicrobial lighting segments, in this example segments 158A-158D, extending around the perimeter of touch screen display surface 150. In this example, the content displayed on touch screen display 150 includes an instruction or informational presentation area indicated generally by reference numeral 156 and a high touch area indicated generally by reference numeral 160. High touch area 160 includes one or more icons 164 with which a user may interact via touch inputs. In this example, a user may make menu selections using the touch icons 164; thus, area 160 around the icons 164 may be considered a "high touch area" in that it is a portion of the display surface 150 that is more likely to be frequently touched by users than, for example, the instruction or informational presentation area 156. In some examples, antimicrobial lighting segments 158A-158D may be controlled such that they illuminate the high touch target area 160 on touch screen display 150 with a higher intensity antimicrobial light, and/or with different wavelengths of antimicrobial light, as compared to relatively lower or less frequently touched areas on display 150, such as informational presentation area 156. In another examples, antimicrobial lighting segments 158A-158D may be controlled such that they illuminate the high touch target area 160 on touch screen display 150 more frequently with antimicrobial light as compared to relatively lower or less frequently touched areas on display 150, such as informational presentation area 156. For these examples, antimicrobial light segments 162A and 162B may be individually controlled to provide such higher intensity and/or more frequent antimicrobial illumination to high touch target area 160. It shall be understood that although FIG. 11 shows a single high touch area 160, that the location and number of high touch areas on a display may vary depending upon the environment in which the display assembly is to be used and/or upon the content to be presented on the touch screen display surface, and that the disclosure is not limited in this respect.

Figure 12:
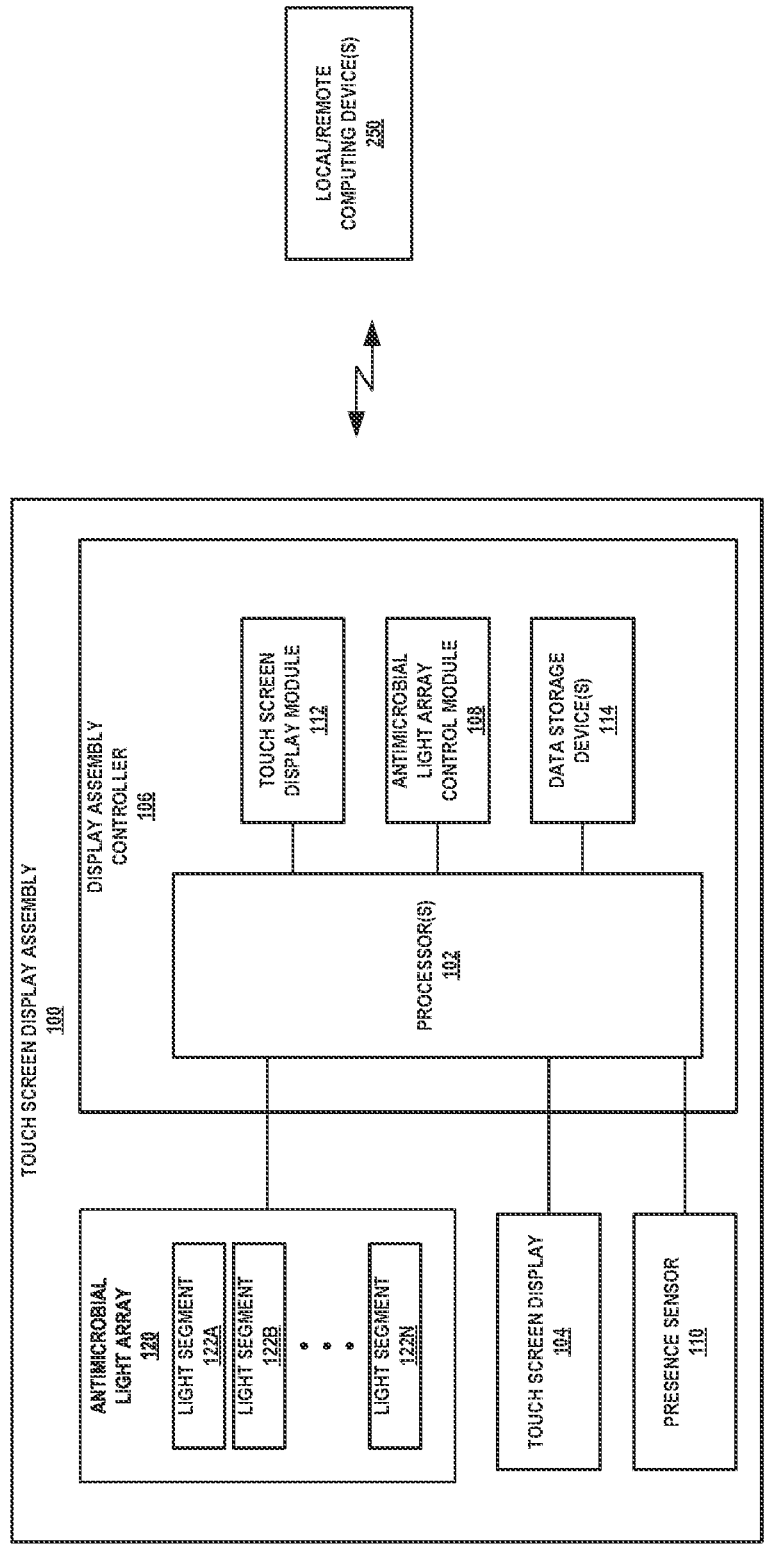
FIG. 12 is a block diagram showing an example touch screen display assembly including an antimicrobial light array for microbial inactivation of touch screen display surface in accordance with the present disclosure.

FIG. 12 is a diagram showing an example touch screen display assembly 100 including an antimicrobial light array 120 for microbial inactivation of a touch screen display surface 104 in accordance with the present disclosure. Example touch screen display assembly 100 includes a touch screen display 104, antimicrobial light array 120 having one or more antimicrobial light segments 122A-122N, a presence sensor 110, and a display assembly controller 106. Display assembly controller 106 includes one or more processors 102, and storage devices including a touch screen display control module 112, an antimicrobial light array control module 108, and data storage 114. In this example, antimicrobial light array 120 is integrated into the touch screen display assembly 100, rather than being retrofittable to an existing touch screen display. Thus, in this example, processor(s) 102 include the touch screen display control software module(s) 112 that controls the functionality of the touch screen display 104 and also includes the antimicrobial light array software control modules 108 that controls functionality of antimicrobial light array 120.

In some examples, it may be desirable to provide substantially evenly distributed antimicrobial illumination across the entire surface area of the touch screen display 204. In such an example, the entire surface area of the touch screen display may be considered the target area. In other examples, it may be desirable to provide relatively higher intensity antimicrobial illumination and/or different wavelengths of antimicrobial light at certain areas or zones within the surface area of the touch screen display, such as those areas or zones on the touch screen display surface that are more frequently touched by users, such as one or more high touch areas 160 as shown in FIG. 11. Other less frequently touched areas or zones within the surface area of the touch screen display surface, such as the instruction area of the display or other areas that are less frequently touched by users, may be provided with relatively lower intensity antimicrobial illumination. It shall be understood, therefore, that the pattern of antimicrobial illumination across the surface area of the touch screen display surface 204 may vary depending upon the application and/or the environment in which the touch screen display assembly 200 is to be used, and that the disclosure is not limited in this respect.

In order to provide varying intensities of antimicrobial illumination at different target areas of a touch screen display 204, the one or more antimicrobial lighting segments 222A-222N in antimicrobial lighting array 220 may be individually controllable. For example, to provide relatively higher intensity antimicrobial lighting to one or more high touch areas of display 204, lighting segments 222A-222N may be individually controlled to provide such higher intensity antimicrobial lighting to the high touch area(s) at one or more predetermined times or upon detection of one or more events.

One such event may include detection of presence of a user near the touch screen display 204. Presence sensor 206 may include one or more of a device that detects the distance, presence, or absence of an object or a user near the touch screen display 204 and/or the touch screen display assembly 200. In one example, the antimicrobial light segments 222A-22N may be controlled to provide high intensity antimicrobial light to the touch screen display surface 204 during periods of high use. In another example, the antimicrobial light segments 222A-22N may be controlled to provide high intensity antimicrobial light to the touch screen display surface 204 in between users.

Touch screen display control module 208 includes computer readable instructions configured to be executed on the one or more processors 202 to enable controller 210 to control functionality of touch screen display 204. For example, array control module 212 may enable controller 210 to receive touch inputs from touch screen display 204, determine what information to present on touch screen display 204, present an interactive display experience to a user on touch screen display 204, etc.

Antimicrobial light array control module 212 includes computer readable instructions configured to be executed on the one or more processors 202 to enable controller 210 to control activation of antimicrobial light segments 222A-222N of light array 220. For example, array control module 212 may enable controller 210 to individually control activation of antimicrobial light segments 222A-222N based on the status information signals received from presence sensor 206. Processor(s) may analyze the received status information signal to determine distance, presence, or absence of a user with respect to the touch screen display assembly 210 and/or the touch screen display 204. For example, one or more of the antimicrobial light segments 222A-222N may be activated to emit antimicrobial light at a first, high setting (that is, highest intensity) at certain times of day or during certain identified periods of use of touch screen display 204 and/or touch screen display assembly 200. As another example, one or more of the antimicrobial light segments 222A-222N may be activated to emit antimicrobial light at a second, low setting (that is, relatively lower intensity than the high setting) during certain times of day or during certain identified periods of use of touch screen display 204 and/or touch screen display assembly 200. As another example, one or more of the antimicrobial light segments 222A-222N may be deactivated so as not to emit antimicrobial light, or be placed in an "off" setting at certain identified times or during certain identified periods of use of touch screen display 204 and/or touch screen display assembly 200. Thus, it shall be understood that antimicrobial light array control module may be programmed to control antimicrobial light array and antimicrobial light array segments in a very flexible manner so as to be customized to the particular environment in which the touch screen display assembly is to be used.

In other examples, the antimicrobial light segments 222A-222N may be controlled by array control module 212 such that one or more of the antimicrobial light segments 222A-222N operate at a high setting, one or more of the antimicrobial light segments 222A-222N operate a lower setting (relatively lower than the high setting), and one or more of the antimicrobial light segments 222A-222N are deactivated or turned off. It shall be understood, therefore, that each of the antimicrobial light segments 222A-222N may be individually controlled by array control module 212 to individually active/deactivate and/or adjust the power and/or intensity of the antimicrobial light output by each antimicrobial light segment 222A-222N, and thus to adjust the irradiance of the antimicrobial light received at the target surface(s).

In other examples, the antimicrobial light segments 222A-222N may be controlled by array control module 212 such that one or more of the antimicrobial light segments 222A-222N emit light within a first antimicrobial wavelength range, one or more of the antimicrobial light segments 122A-122N emit light within a second antimicrobial wavelength range, and/or one or more of the antimicrobial light segments 122A-122N are deactivated or turned off. It shall be understood, therefore, that each of the antimicrobial light segments 222A-222N may be individually controlled by array control module 212 to individually control the wavelength of the antimicrobial light output by antimicrobial light array 220, and thus to adjust the wavelength(s) of antimicrobial light received at the target surface(s).

Antimicrobial light array 220 may be controlled in response to inputs from a user. For example, through touch screen display 204, an authorized user may input the desired settings (e.g., high, modified, off, etc.) for some or all of the antimicrobial light segments 222A-222N. These inputs, received through touch screen display module 208, may cause processor to update internal settings or operational parameters for the antimicrobial light array 220.

Processor(s) 202 may control antimicrobial light array 220 based on signals received from touch screen display module 208. For example, array control module 212 may analyze the signals received form the touch screen display module 212 to individually control activation of selected antimicrobial light segments 222A-222N at the appropriate setting(s) based on whether or not the touch screen display in currently in use or the amount of time in between users of the touch screen display. For example, a relatively shorter amount of time between users of the touch screen display may be indicative of the relative "busy-ness" of the restaurant or other environment in which the touch screen display in being used, as there will be a smaller amount of down or idle time between users when a restaurant is busy as compared to when the restaurant is not as busy.

As another example, processor(s) 202 may control antimicrobial lighting system 100 may be controlled based on the time and/or date. For example, array control module 108 may determine the date and time to determine whether the current time corresponds to a heavy usage time of the touch screen display assembly 200 or to a reduced or standby usage time. For example, it may be desirable to operate the antimicrobial light segments 222A-222N on a high setting at night or other time(s) when the restaurant is closed, for example.

Antimicrobial lighting system 100 may be manually controlled by a user, such as through user interface 104 or one or more of computing device(s) 140. For example, housekeeping or other authorized staff may manually activate and/or control antimicrobial lighting array 220 during routine cleaning procedures. As another example, a service technician or custodian may manually activate and/or control antimicrobial lighting array 220 during a service call. As another example, touch screen display assembly may be configured for wired or wireless communication with one or more remote or local computing device(s) 300. In such examples, housekeeping, front desk staff, service technician or other authorized user may manually activate antimicrobial lighting system remotely via one or more remote or local computing device(s) 300. In addition, information concerning operation of the antimicrobial light array and the touch screen display 204 may be sent to one or more of the remote or local computing device(s) 300. This information may include a record of the dates, times, settings, and duration of each antimicrobial lighting treatment applied to the touch screen display surface(s), status information concerning the relative lifetime of the antimicrobial lighting segments or individual lighting elements in the antimicrobial light array 220, and/or any other information that may be relevant for monitoring and/or managing antimicrobial light treatments of the individual touch screen display surface 204 or of a plurality of similar touch screen display surfaces disposed at the location or at multiple locations associated with a corporate entity.

Figure 13:
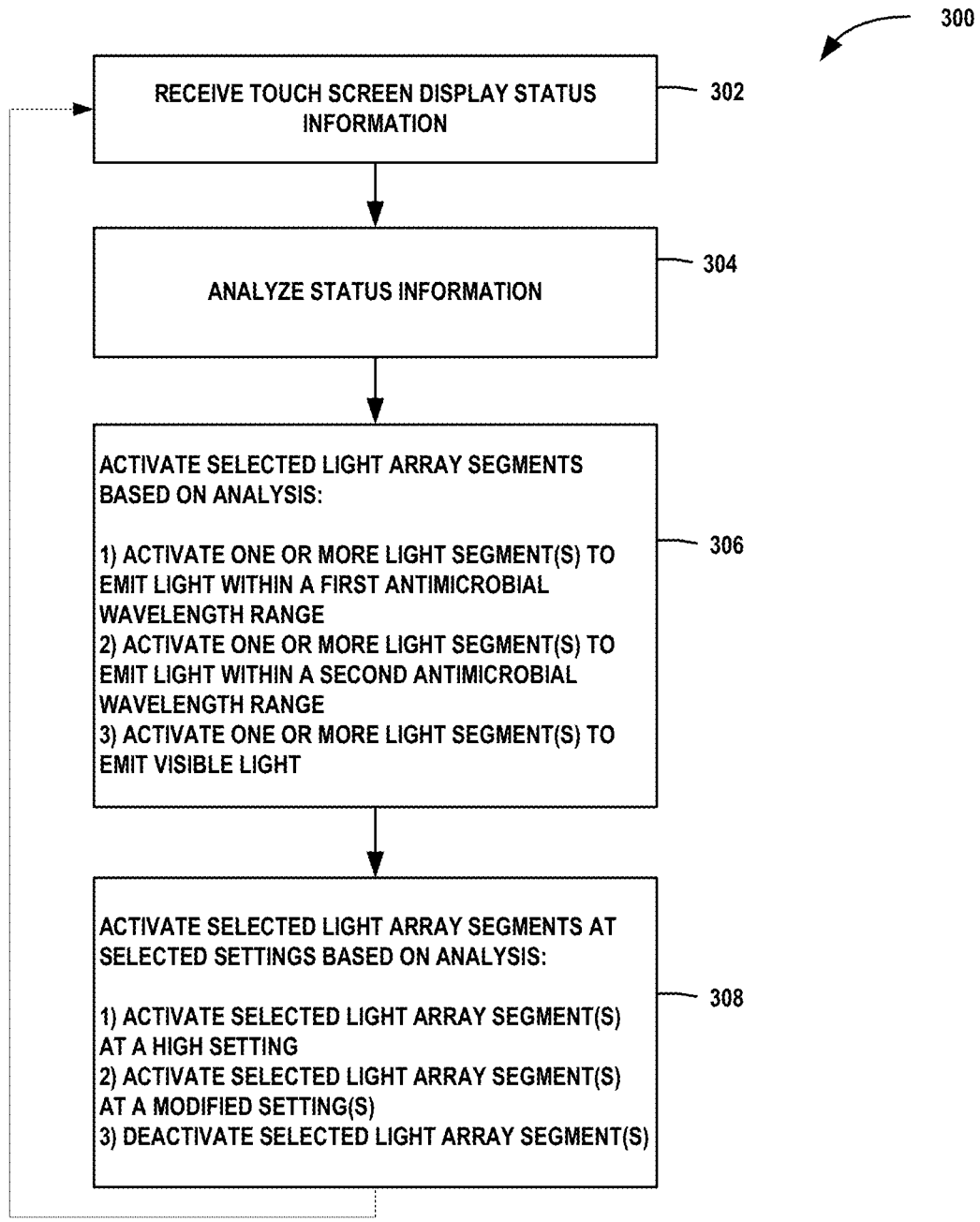
FIG. 13 is a flowchart illustrating an example process 350 by which a computing device may individually control one or more antimicrobial light segments to apply an antimicrobial light treatment to a touch screen display surface in accordance with the present disclosure.

FIG. 13 is a flowchart illustrating an example process 300 by which a computing device (such as display assembly controller 210 of FIG. 12) may individually control one or more antimicrobial light segments (such as antimicrobial light segments 222A-222N) in accordance with the present disclosure. In the example of FIG. 13, a computing device (such as display assembly controller 210) receives touch screen display status information (352). For example, the touch screen display status information may be received from a presence sensor 206, touch screen display module 208, an internal timer, etc. The status information may include information concerning user presence or non-presence near the touch screen display, the time of day, whether the touch screen display is in currently in use, the relative "busy-ness" of the touch screen display, or other relevant status information concerning the touch screen display.

The computing device analyzes the status information to determine how to individually control each of the antimicrobial light segments (304). For example, the computing device may activate one or more light segments that emit light within a first antimicrobial wavelength range, activate one or more light segments that emit light within a second antimicrobial wavelength range, and/or activate one or more light segments that emit light within the visible spectrum (306). As another example, the computing device may determine that some or all of the antimicrobial light segments should be activated at a high or maximum setting; the computing device may determine that some or all of the antimicrobial light segments should be activated at a modified or reduce setting(s); and/or the computing device may determine that some or all of the light segments should be deactivated (308).

Additional Examples

Example 1: A lighting array comprising a fixture, and one or more antimicrobial lighting segments mounted on the lighting fixture, each antimicrobial lighting segment including one or more elements, wherein each element emits light at a wavelength, irradiance, and direction sufficient to inactivate one or more microorganisms on a target area of a touch screen display surface.

Example 2: The system of Example 1 wherein the lighting array controls each antimicrobial light segment is controlled based on touch screen display surface usage information.

Example 3: The system of Example 1 wherein the lighting array deactivates at least some of the antimicrobial lighting segments when the touch screen display surface usage information is indicative of presence of a user.

Example 4: The system of Example 1 wherein each of the one or more antimicrobial lighting segments are individually controllable by the lighting array such that each lighting segment may be activated at a first, high setting, a second, modified setting, or a third, deactivated setting independently of the other one or more antimicrobial lighting segments.

Example 5: The system of Example 1 wherein the system further comprises a presence sensor that detects presence of a user near the touch screen display surface.

Example 6: The system of Example 1 wherein the lighting array further controls the one or more antimicrobial lighting segments based on the time of day.

Example 7: The system of Example 1 wherein the touch screen display surface includes a plurality of target zones, and wherein the one or more antimicrobial lighting segments are individually controllable to direct light at the wavelength and irradiance sufficient to inactivate one or more microorganisms within one or more of the target zones.

Example 8: The lighting system of Example 1 wherein each antimicrobial lighting segment includes a substrate and a plurality of light-emitting diode (LED) elements, and wherein each LED element emits light including wavelengths in a range of about 405±15 nanometers.

Example 9: The lighting system of Example 1 wherein the lighting array further includes one or more lighting elements that emit light having a wavelength range in the visible spectrum.

Example 10: The lighting system of Example 1, wherein each antimicrobial lighting segment includes a substrate and a plurality of light-emitting diode (LED) elements, wherein one or more of the LED elements emit light within a first antimicrobial wavelength range of about 380-420 nanometers, and one or more of the LED elements emit light within a second antimicrobial wavelength range of about 200-280 nanometers.

Example 11: The lighting system of Example 1, wherein each antimicrobial lighting segment includes a substrate and a plurality of light-emitting diode (LED) elements, wherein one or more of the LED elements emit light within a first antimicrobial wavelength range of about 380-420 nanometers and one or more of the LED elements emit light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm or ultraviolet C (UVC) light within a wavelength range of 200-280 nm.

Example 12: The lighting system of Example 1 wherein the one or more microorganisms include at least one of *Listeria monocytogenes*, enterohemorrhagic *Escherichia coli*, *Salmonella*, and *Staphylococcus aureus*.

Example 13: An antimicrobial lighting assembly comprising a frame assembly configured for mounting around at least a portion of the perimeter of a touch screen display surface; and one or more antimicrobial lighting segments mounted on the frame assembly, each antimicrobial lighting segment including one or more antimicrobial lighting elements, wherein each antimicrobial lighting element emits light at a wavelength, irradiance, and direction sufficient to inactivate one or more microorganisms on a target area of the touch screen display surface.

Example 14: The antimicrobial lighting assembly of Example 11 wherein the frame assembly is mounted around the entire perimeter of the touch screen display surface.

Example 15: The antimicrobial lighting assembly of Example 11 further comprising a sensor that detects presence of a user near the touch screen display, and wherein power to the antimicrobial lighting segments is deactivated upon detection of presence of the user.

Example 16: The antimicrobial lighting assembly of Example 15 wherein, subsequent to detection of presence of a user near the touch screen display, the sensor detects that the user is no longer present near the touch screen display, and wherein power to the antimicrobial lighting segments is activated.

Example 17: The antimicrobial lighting assembly of Example 13 wherein the frame assembly is configured to mount on a bezel of the touch screen display.

Example 18: The antimicrobial lighting assembly of Example 13 wherein the frame assembly is configured for retrofittable mounting around the perimeter of a touch screen display surface.

Example 19: The antimicrobial lighting assembly of Example 13, wherein each antimicrobial lighting segment includes a substrate and a plurality of light-emitting diode (LED) elements, wherein one or more of the LED elements emit light within a first antimicrobial wavelength range of about 380-420 nanometers, and one or more of the LED elements emit light within a second antimicrobial wavelength range of about 200-280 nanometers.

Example 20: The antimicrobial lighting assembly of Example 13, wherein each antimicrobial lighting segment includes a substrate and a plurality of light-emitting diode (LED) elements, wherein one or more of the LED elements emit light within a first antimicrobial wavelength range of about 380-420 nanometers and one or more of the LED elements emit light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm or ultraviolet C (UVC) light within a wavelength range of 200-280 nm.

Example 17: A touch screen display assembly comprising a touch screen display configured for interaction with one or more users; a housing configured to receive the touch screen display; an antimicrobial lighting assembly mounted within the housing and comprising one or more antimicrobial lighting segments, each antimicrobial lighting segment including one or more antimicrobial lighting elements, wherein each antimicrobial lighting element emits light at a wavelength, irradiance, and direction sufficient to inactivate one or more microorganisms on a target area of the touch screen display surface, each of the one or more antimicrobial lighting segment mounted along at least a portion of an edge of the touch screen display so as to emit antimicrobial light in a direction to inactivate microorganisms on a target area of the touch screen display surface.

Example 18: The touch screen display assembly of Example 17 wherein the housing comprises one of a kiosk, a touch screen display monitor housing, or a video wall rack.

Example 19: The touch screen display assembly of Example 17 wherein each of the one or more antimicrobial lighting elements has a beam angle in the range of 12° to 60°.

Example 20: The touch screen display assembly of Example 17 wherein a first subset of the at least one or more antimicrobial lighting elements have a first beam angle and a second subset of the at least one or more antimicrobial lighting elements have a second beam angle that is different than the first beam angle.

Example 21: The touch screen display assembly of Example 17 wherein each antimicrobial lighting segments includes a stacked arrangement of antimicrobial lighting segments, such that a first stack of antimicrobial lighting segments is mounted on the bezel of the touch screen display surface and a second stack of antimicrobial lighting segments is mounted above the first stack of antimicrobial lighting segments.

Example 22: The touch screen display assembly of Example 17 further comprising a controller that receives one or more signals usable to determine status information concerning the touch screen display and controls the antimicrobial lighting segments based on the determined status information concerning the touch screen display.

Example 23: The touch screen display assembly of Example 22 where the controller further receives one or more signals usable to determine presence of a user and controls the one or more antimicrobial lighting segments based on whether or not a user is present.

Example 24: The touch screen display assembly of Example 22 where the controller further individually controls each antimicrobial lighting segment based on the received status information concerning the touch screen display.

Example 25: The touch screen display assembly of Example 22 where the controller further individually controls each antimicrobial lighting segment to provide antimicrobial illumination to one or more target areas on the touch screen display surface based on the received status information concerning the touch screen display.

Example 26: The touch screen display assembly of Example 17 further comprising a controller that receives one or more signals usable to determine status information concerning the touch screen display and individually controls the one or more antimicrobial lighting segments to provide antimicrobial illumination to one or more high touch target areas on the touch screen display.

Example 27: The touch screen display assembly of Example 17, wherein each antimicrobial lighting segment includes a substrate and a plurality of light-emitting diode (LED) elements, wherein one or more of the LED elements emit light within a first antimicrobial wavelength range of about 380-420 nanometers, and one or more of the LED elements emit light within a second antimicrobial wavelength range of about 200-280 nanometers.

Example 28: The touch screen display assembly of Example 17, wherein each antimicrobial lighting segment includes a substrate and a plurality of light-emitting diode (LED) elements, wherein one or more of the LED elements emit light within a first antimicrobial wavelength range of about 380-420 nanometers and one or more of the LED elements emit light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm or ultraviolet C (UVC) light within a wavelength range of 200-280 nm.

Various examples have been described. These and other examples are within the scope of the following claims.

The invention claimed is:

1. A lighting assembly comprising:
a fixture;
one or more antimicrobial lighting segments mounted on the fixture, each of the antimicrobial lighting segments including one or more elements, wherein each of the elements emits light at a wavelength, irradiance, and direction sufficient to inactivate one or more microorganisms on a target area of a touch screen display surface, wherein the target area includes at least one high touch target area and at least one lower touch target area, and wherein the one or more antimicrobial lighting elements includes a first stack of antimicrobial lighting elements mounted on the fixture and a second stack of antimicrobial lighting elements mounted above the first stack of antimicrobial lighting elements; and a controller configured to individually control the one or more antimicrobial lighting segments to provide at least one of relatively higher intensity antimicrobial illumination or more frequent antimicrobial illumination to the at least one high touch target area as compared to the lower touch target area.

2. The lighting assembly of claim 1, wherein the controller controls each of the antimicrobial lighting segments based on touch screen display surface usage information.

3. The lighting assembly of claim 1, wherein each of the one or more antimicrobial lighting segments is individually controllable by the controller such that each of the antimicrobial lighting segments may be activated at a first, highest setting, a second, modified setting, or a third, deactivated setting independently of each other one of the antimicrobial lighting segments.

4. The lighting assembly of claim 1, wherein the lighting assembly further comprises a presence sensor that detects presence of a user near the touch screen display surface.

5. The lighting assembly of claim 4, wherein the controller deactivates at least some of the antimicrobial lighting segments based on detection of presence of the user near the touch screen display surface.

6. The lighting assembly of claim 1, wherein the controller controls the one or more antimicrobial lighting segments based on time of day.

7. The lighting assembly of claim 1, wherein the target area includes a plurality of target zones, and wherein the one or more antimicrobial lighting segments are individually controllable to direct light at the wavelength and irradiance sufficient to inactivate the one or more microorganisms within one or more of the target zones.

8. The lighting assembly of claim 1, wherein each of the antimicrobial lighting segments includes a substrate and a plurality of light-emitting diode (LED) elements, and wherein each of the LED elements emits light including wavelengths in a range of about 405±15 nanometers.

9. The lighting assembly of claim 1, wherein the lighting assembly further includes one or more lighting elements that emit light having a wavelength range in a visible spectrum.

10. The lighting assembly of claim 1, wherein each of the antimicrobial lighting segments includes a substrate and a plurality of light-emitting diode (LED) elements, wherein one or more of the LED elements emit light within a first antimicrobial wavelength range of about 380-420 nanometers, and one or more of the LED elements emit light within a second antimicrobial wavelength range of about 200-280 nanometers.

11. The lighting assembly of claim 1, wherein each of the antimicrobial lighting segments includes a substrate and a plurality of light-emitting diode (LED) elements, wherein one or more of the LED elements emit light within a first antimicrobial wavelength range of about 380-420 nanometers and one or more of the LED elements emit light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm or ultraviolet C (UVC) light within a wavelength range of 200-280 nm.

12. The lighting assembly of claim 1, wherein the one or more microorganisms include at least one of *Listeria monocytogenes*, enterohemorrhagic *Escherichia coli*, *Salmonella*, and *Staphylococcus aureus*.

13. An antimicrobial lighting assembly comprising:

a frame assembly configured for mounting around at least a portion of a perimeter of a touch screen display surface;

one or more antimicrobial lighting segments mounted on the frame assembly, each of the antimicrobial lighting segments including one or more antimicrobial lighting elements, wherein each of the antimicrobial lighting elements emits light at a wavelength, irradiance, and direction sufficient to inactivate one or more microorganisms on a target area of the touch screen display surface, wherein the target area includes at least one high touch target area and at least one lower touch target area, and wherein the one or more antimicrobial lighting elements includes a first stack of antimicrobial lighting elements mounted on the frame assembly and a second stack of antimicrobial lighting elements mounted above the first stack of antimicrobial lighting elements; and a controller configured to individually control the one or more antimicrobial lighting segments to provide at least one of relatively higher intensity antimicrobial illumination or more frequent antimicrobial illumination to the at least one high touch target area as compared to the lower touch target area.

14. The antimicrobial lighting assembly of claim 13, wherein the frame assembly is configured for mounting around the entire perimeter of the touch screen display surface.

15. The antimicrobial lighting assembly of claim 13, further comprising a sensor that detects presence of a user near the touch screen display surface, and a controller that deactivates the antimicrobial lighting segments upon detection of presence of the user.

16. The antimicrobial lighting assembly of claim 15, wherein, subsequent to detection of presence of the user near the touch screen display surface, in response to detection that the user is no longer present near the touch screen display surface, the controller activates the antimicrobial lighting segments.

17. The antimicrobial lighting assembly of claim 13, wherein the frame assembly is configured to mount on a bezel of the touch screen display surface.

18. The antimicrobial lighting assembly of claim 13, wherein the frame assembly is configured for retrofittable mounting around the perimeter of the touch screen display surface.

19. The antimicrobial lighting assembly of claim 13, wherein each of the antimicrobial lighting segments includes a substrate and a plurality of light-emitting diode (LED) elements, wherein one or more of the LED elements emit light within a first antimicrobial wavelength range of about 380-420 nanometers, and one or more of the LED elements emit light within a second antimicrobial wavelength range of about 200-280 nanometers.

20. The antimicrobial lighting assembly of claim 13, wherein each of the antimicrobial lighting segments includes a substrate and a plurality of light-emitting diode (LED) elements, wherein one or more of the LED elements emit light within a first antimicrobial wavelength range of about 380-420 nanometers and one or more of the LED elements emit light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm or ultraviolet C (UVC) light within a wavelength range of 200-280 nm.

21. A touch screen display assembly comprising:
a touch screen display configured for interaction with one or more users;
a housing configured to receive the touch screen display;
an antimicrobial lighting assembly mounted within the housing and comprising one or more antimicrobial lighting segments, each of the antimicrobial lighting segments including one or more antimicrobial lighting elements, wherein each of the antimicrobial lighting elements emits light at a wavelength, irradiance, and direction sufficient to inactivate one or more microorganisms on a target area of a surface of the touch screen display, wherein the one or more antimicrobial lighting elements includes a first stack of antimicrobial lighting elements mounted within the housing and a second stack of antimicrobial lighting elements mounted above the first stack of antimicrobial lighting elements,
each of the one or more antimicrobial lighting segments mounted along at least a portion of an edge of the touch screen display so as to emit antimicrobial light in a direction to inactivate microorganisms on the target area of the surface of the touch screen display, wherein the target area includes at least one high touch target area and at least one lower touch target area; and
a controller configured to individually control the one or more antimicrobial lighting segments to provide at least one of relatively higher intensity antimicrobial illumination or more frequent antimicrobial illumination to the at least one high touch target area as compared to the lower touch target area.

22. The touch screen display assembly of claim 21, wherein the housing comprises one of a kiosk, a touch screen display monitor housing, or a video wall rack.

23. The touch screen display assembly of claim 21, wherein each of the one or more antimicrobial lighting elements has a beam angle in the range of 12° to 60°.

24. The touch screen display assembly of claim 21, wherein a first subset of the one or more antimicrobial lighting elements have a first beam angle and a second subset of the one or more antimicrobial lighting elements have a second beam angle that is different than the first beam angle.

25. The touch screen display assembly of claim 21, wherein the one or more antimicrobial lighting segments comprises a first stack of antimicrobial lighting segments mounted on the bezel of the surface of the touch screen display and a second stack of antimicrobial lighting segments mounted above the first stack of antimicrobial lighting segments.

26. The touch screen display assembly of claim 21, wherein the controller is configured to receive one or more signals usable to determine status information concerning the touch screen display and to control the antimicrobial lighting segments based on the determined status information concerning the touch screen display.

27. The touch screen display assembly of claim 26, wherein the controller is further configured to receive one or more signals usable to determine presence of a user and to control the one or more antimicrobial lighting segments based on whether or not the user is present.

28. The touch screen display assembly of claim 26, wherein the controller is further configured to individually control each of the antimicrobial lighting segments based on the status information concerning the touch screen display.

29. The touch screen display assembly of claim 26, wherein the target area includes one or more target areas, wherein the controller further individually controls each of the antimicrobial lighting segments to provide antimicrobial illumination to the one or more target areas on the surface of the touch screen display based on the status information concerning the touch screen display.

30. The touch screen display assembly of claim 21, wherein the controller is configured to receive one or more signals usable to determine status information concerning the touch screen display and to individually control the one or more antimicrobial lighting segments to provide antimicrobial illumination to the at least one high touch target area of the touch screen display.

31. The touch screen display assembly of claim 21, wherein each of the antimicrobial lighting segments includes a substrate and a plurality of light-emitting diode (LED) elements, wherein one or more of the LED elements emit light within a first antimicrobial wavelength range of about 380-420 nanometers, and one or more of the LED elements emit light within a second antimicrobial wavelength range of about 200-280 nanometers.

32. The touch screen display assembly of claim 21, wherein each of the antimicrobial lighting segments includes a substrate and a plurality of light-emitting diode (LED) elements, wherein one or more of the LED elements emit light within a first antimicrobial wavelength range of about 380-420 nanometers and one or more of the LED elements emit light within a second antimicrobial wavelength range, wherein the second antimicrobial wavelength range includes at least one of ultraviolet A (UVA) light within a wavelength range of 315-400 nm, ultraviolet B (UVB) light within a wavelength range of 280-315 nm or ultraviolet C (UVC) light within a wavelength range of 200-280 nm.

* * * * *